(12) United States Patent
Ueda

(10) Patent No.: US 8,512,758 B2
(45) Date of Patent: Aug. 20, 2013

(54) POWDER COMPOSITION

(75) Inventor: Fumitaka Ueda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 293 days.

(21) Appl. No.: 12/676,685

(22) PCT Filed: Sep. 3, 2008

(86) PCT No.: PCT/JP2008/066270
§ 371 (c)(1),
(2), (4) Date: Mar. 5, 2010

(87) PCT Pub. No.: WO2009/031694
PCT Pub. Date: Mar. 12, 2009

(65) Prior Publication Data
US 2010/0209523 A1    Aug. 19, 2010

(30) Foreign Application Priority Data
Sep. 7, 2007    (JP) .................. 2007-232793

(51) Int. Cl.
*A61K 9/16* (2006.01)
*A61K 9/14* (2006.01)
*A61K 31/715* (2006.01)
*C08B 37/16* (2006.01)

(52) U.S. Cl.
USPC ............ 424/498; 514/54; 514/58; 424/489; 536/103

(58) Field of Classification Search
None
See application file for complete search history.

(56) References Cited

U.S. PATENT DOCUMENTS

| | | | |
|---|---|---|---|
| 6,180,139 B1 | 1/2001 | Hsia et al. | |
| 7,737,269 B2 * | 6/2010 | Reuscher et al. | 536/103 |
| 7,780,873 B2 * | 8/2010 | Mora-Gutierrez et al. | 252/400.21 |
| 2003/0199576 A1 * | 10/2003 | Lee et al. | 514/474 |
| 2004/0115309 A1 * | 6/2004 | Harris | 426/72 |
| 2006/0135475 A1 * | 6/2006 | Reuscher et al. | 514/58 |
| 2008/0020995 A1 * | 1/2008 | Purpura et al. | 514/58 |
| 2008/0160137 A1 * | 7/2008 | Kon et al. | 426/74 |

FOREIGN PATENT DOCUMENTS

| | | |
|---|---|---|
| CA | 2 546 464 A1 | 11/2006 |
| DE | 199 20 316 A1 | 12/1999 |
| GB | 743600 A | 1/1956 |
| JP | 54109962 A | 8/1979 |
| JP | 05-038273 A | 2/1993 |
| JP | 799932 A | 4/1995 |
| JP | 2000-106844 A | 4/2000 |
| JP | 2000-125811 A | 5/2000 |
| JP | 2000-189102 A | 7/2000 |
| JP | 2004-530407 A | 10/2004 |
| JP | 2005343880 A | 12/2005 |
| WO | WO 98/33494 * | 8/1998 |
| WO | WO 02/24002 * | 3/2002 |
| WO | 03/011054 A1 | 2/2003 |
| WO | 2007026474 A1 | 3/2007 |
| WO | 2007/079443 A2 | 7/2007 |

OTHER PUBLICATIONS

Abstract of JP 2-265458 A, 1990, pp. 1, vol. 49, No. 90, World Patent Information, Derwent, GB, XP 002082644.
Packer, L., "The Antioxidant Miracle", Kodansha Ltd., Jun. 2002, pp. 36-37, 53-55.
Bjelakovic, G., et al., "Mortality in Randomized Trials of Antioxidant Supplements for Primary and Secondary Prevention: Systematic Review and Meta-analysis", Journal of the American Medical Association, Feb. 2007, pp. 842-857, vol. 297, No. 8.
Communication dated Nov. 27, 2012 from the Japanese Patent Office in counterpart Japanese application No. 2007-232793.
Office Action issued on Jan. 7, 2013, from the State Intellectual Property Office of the P.R. China in counterpart Chinese Application No. 200880115103.5.
Office Action issued on Apr. 5, 2012 from the Chinese Patent Office in Chinese Application No. 200880115103.5.
Office Action issued Apr. 23, 2013, from the Japanese Patent Office in corresponding Japanese Application No. 2007-232793.

* cited by examiner

*Primary Examiner* — Robert A Wax
*Assistant Examiner* — Jeffrey T Palenik
(74) *Attorney, Agent, or Firm* — Sughrue Mion, PLLC

(57) ABSTRACT

A powder composition, includes: (A) an oil-soluble antioxidant substance powder; (B) a water-soluble antioxidant substance powder; and (C) at least one of zinc, selenium, manganese and copper.

6 Claims, No Drawings

POWDER COMPOSITION

CROSS REFERENCE TO RELATED APPLICATIONS

This application is the 371 National Stage entry for International Application PCT/JP2008/066270, filed 3 Sep. 2008. This application claims priority to Japanese Patent Application No 2007-232793, filed 7 Sep. 2007. The disclosures of the above applications are incorporated herein by reference in their entirety.

TECHNICAL FIELD

The present invention relates to a powder composition and more specifically, to a powder composition containing antioxidant substances.

BACKGROUND ART

Active oxygens are deeply involved in biophylaxis and signal systems between cells in the living body but, on the other hand, it has been revealed that active oxygens cause various oxidative damages on tissues and components of the living body and thus active oxygens damage human health and cause acceleration of aging speed.

As the active oxygens, there are radical species such as a superoxide anion (.O2-), a hydroxyl radical (.OH—), a hydroperoxyl radical (.OOH), an alkoxyl radical (LO.), and an alkylperoxyl radical (LOO.) which are formed by reduction of a part of oxygen at the time when mitochondria produces energy within cells in the living body through metabolism of oxygen, and non-radical species such as hydrogen peroxide (H2O2) formed from the superoxide anion, singlet oxygen (1O2), peroxy nitrite (ONOO—), lipid hydroperoxide (LOOH), and hypochlorous acid (HOCl).

It is known that these active oxygens may damage DNA's and body tissues to cause development of malignant tumors and may cause ischemic diseases such as cardiac infarction and angina, liver damage, cerebrovascular disorder, Alzheimer type dementia, diabetes, gout, nephritis, cataract, blotches on skin, wrinkles, and freckles.

Since the prevention of the damage caused by the toxicity of these active oxygens may lead to prophylaxis of these diseases, many antioxidant substances having active oxygen-removing ability have been proposed.

However, in an epidemiological survey on the relation between ingestion of antioxidant supplements (vitamins A, C, and E, β-carotene, selenium) and death disclosed in Journal of the American Medical Association published on Feb. 28, 2007, there is a report that mortality of persons who ingest the supplements other than vitamin C or selenium rather increases. Thus, it has been increasingly widely recognized that continuous ingestion of single antioxidant substance is bad since such ingestion breaks down the antioxidation balance in the living body (see Journal of American Medical Association, Vol. 297, No. 8).

The human body is separated into oil-soluble parts represented by cell membranes and water-soluble parts such as cytoplasm and blood, and there are reports that a preferable effect is obtained by combining a plurality of antioxidant substances (JP-A-2000-189102 and JP-A-2004-530407).

Particularly, an antioxidation network is present within the body and it is said that mainly thioctic acid has an action of recycling water-soluble and oil-soluble antioxidant substances and improving the life of their effectiveness (Antioxidant Miracle (written by Lester Packer, published on Jun. 20, 2002, Kodansha Ltd.)).

Moreover, there are antioxidant enzymes having action to counter active oxygens, such as superoxide dismutase and glutathion peroxidase. They use selenium, zinc, manganese, or copper, which is called an antioxidant mineral, as an active site and the antioxidant enzymes can be activated by ingesting individual minerals. Furthermore, by ingesting them together with the above water-soluble and oil-soluble antioxidant substances, it is possible to improve the antioxidation balance in the body.

The minerals are used as inorganic salts but recently, they are provided in the form of a mineral yeast wherein a mineral is incorporated into a yeast to aim at improvement in stability and increase in absorption efficiency (JP-A-2000-125811).

DISCLOSURE OF THE INVENTION

As mentioned above, it is requested to use an oil-soluble antioxidant substance and a water-soluble antioxidant substance in combination. However, even when an oil-soluble antioxidant substance, a yeast, and a mineral of an inorganic salt and a water-soluble antioxidant substance, which are not miscible under ordinary circumstances, are mixed as they are and included in soft capsules or the like, it has been found that they are not dispersed in the body and absorption thereof becomes worse. Moreover, when different antioxidant ingredients having high reactivity are present in a mixed state, there arise a new problem that the antioxidant ingredients are reacted with each other and are deteriorated.

The invention improves absorbability into the body and storage stability of the oil-soluble antioxidant substance and the water-soluble antioxidant substance at the time when the antioxidant substances are used.

The invention solves the above various problems by transforming the antioxidant substances having different properties into individual separate powders.

The invention consists of the following constitution.

(1) A powder composition, comprising:
 (A) an oil-soluble antioxidant substance powder;
 (B) a water-soluble antioxidant substance powder; and
 (C) at least one of zinc, selenium, manganese and copper.

(2) The powder composition as described in (1) above,
wherein (A) the oil-soluble antioxidant substance powder contains at least one of a carotinoid pigment, a fat-soluble vitamin and a fat-soluble vitamin-like substance.

(3) The powder composition as described in (1) or (2) above,
wherein (A) the oil-soluble antioxidant substance powder contains a carotinoid pigment, the carotinoid pigment being a natural extract containing astaxanthin or an ester of astaxanthin.

(4) The powder composition as described in any one of (1) to (3) above,
wherein (A) the oil-soluble antioxidant substance powder contains a fat-soluble vitamin-like substance, the fat-soluble vitamin-like substance being ubidecarenone.

(5) The powder composition as described in any one of (1) to (4) above,
wherein (A) the oil-soluble antioxidant substance is a powder composition obtained by drying an emulsion composition containing: (a) at least one of a sucrose fatty acid ester and a polyglycerin fatty acid ester; and (b) a phospholipid, wherein mass composition ratios of (a) and (b) are the same or the mass composition ratio of (a) is larger than the mass composition ratio of (b).

(6) The powder composition as described in any one of (1) to (5) above,
wherein (B) the water-soluble antioxidant substance contains at least one of vitamin C, a catechin and a flavonoid.

(7) The powder composition as described in any one of (1) to (6) above,
wherein (B) the water-soluble antioxidant substance is an oil-coated powder.

(8) The powder composition as described in any one of (1) to (7) above, further comprising:
a cyclodextrin/thioctic acid complex.

(9) The powder composition as described in any one of (1) to (8) above, comprising:
a mineral yeast that contains (C) the at least one of zinc, selenium, manganese and copper.

BEST MODE FOR CARRYING OUT THE INVENTION

The powder composition of the invention comprises (A) an oil-soluble antioxidant substance powder, (B) a water-soluble antioxidant substance powder, and (C) at least one of zinc, selenium, manganese, and copper. (A) Oil-soluble antioxidant substance powder The powder composition of the invention contains at least one oil-soluble antioxidant substance.

As the oil-soluble antioxidant substance for use in the invention, there may be mentioned carotinoids (carotinoid pigments) and also fat-soluble vitamins, fat-soluble vitamin-like substances, and the like having antioxidant activity. There may be mentioned carotinoids, fat-soluble vitamins, fat-soluble vitamin-like substances (ubiquinones, ω-3 oils and fats (oils and fats including EPA, DHA, linoleic acid, etc.)), and the like to be described below.

By containing the oil-soluble antioxidant substance in a powder form, dispersibility and absorbability thereof are improved even when it is mixed with the water-soluble antioxidant substance and also stability at storage with time is improved. Preferably, the oil-soluble antioxidant substance is finely emulsified and powdered.

Carotinoids

As the carotinoids in the invention, carotinoids including natural pigments can be preferably mentioned. They are yellow to red terpenoid pigments, including those derived from plants, algae, and bacteria.

Moreover, they are not limited to naturally occurring ones, and anyone is included in the carotinoids in the invention so far as it is obtained according to usual methods. For example, most of carotenes of the carotinoids to be described below are also produced by synthesis and most of commercial β-carotenes are produced by synthesis.

As such carotinoids, hydrocarbons (carotenes) and oxidized alcohol derivatives thereof (xanthophylls) may be mentioned. Of these, there may be preferably mentioned actinioerythrol, astaxanthin, bixin, canthaxanthin, capsanthin, capsorbin, β-apo-8'-carotenal (apocarotenal), β-12'-apocarotenal, α-carotene, β-carotene, "carotene" (a mixture of α- and β-carotenes), γ-carotene, β-criptoxanthin, lutein, lycopene, violerythrin, zeaxanthin, and esters of those having a hydroxyl or carboxyl among them. Particularly preferably mentioned is a natural extract containing astaxanthin or an ester thereof.

Most of the carotinoids are present in cis and trans isomer forms but synthesized products are frequently racemic mixtures.

The carotinoids can be generally extracted from plant raw materials. These carotinoids have various functions. For example, lutein extracted from petals of marigold is widely used as a raw material of feed for poultry and has a function of coloring skin and fat of poultry and eggs laid by poultry.

The carotinoids for use in the invention are preferably in an oil form at ordinary temperature from the viewpoint of handling. Particularly preferred is at least one selected from astaxanthin and derivatives thereof such as esters of astaxanthin (hereinafter generically named as "astaxanthins") which have an antioxidant effect, an antiinflammatory effect, a skin antiaging effect, and a whitening effect and are known as colorants ranging from yellow to red.

Astaxanthin is a red pigment having absorption maximum at 476 nm (ethanol) or 468 nm (hexane) and belongs to one kind of carotinoids, xanthophyll (Davies, B. H.: In "Chemistry and Biochemistry of Plant Pigments", T. W. Goodwin ed., 2nd ed., 38-165, Academic Press, NY, 1976). The chemical structure of astaxanthin is 3,3,'-dihydroxy-β,β-carotene-4,4'-dione (C40H52O4, molecular weight 596.82).

With regard to astaxanthin, three isomers of 3S,3S'-isomer, 3S,3R'-isomer (meso-isomer), and 3R,3R'-isomer are present in terms of configuration of the hydroxyl group at 3(3')-position of the ring structures present at both ends of the molecule. Moreover, cis- and trans-isomers are further present in terms of the conjugate double bonds at the central part of the molecule. For example, all cis-isomer, 9-cis-isomer, 13-cis-isomer, and the like are present.

The above hydroxyl group at the 3(3')-position can form an ester with a fatty acid. The astaxanthin obtained from krill contains a diester having two fatty acids combined therewith (Yamaguchi, K., Miki W., Toriu, N., Kondo, Y., Murakami M., Konosu, S., Satake, M., Fujita, T.: The composition of carotenoid pigments in the antarctic krill *Euphausia superba*, Bull. Jap. Sos. Sci. Fish., 1983, 49, p. 1411-1415.), and one obtained from *H. pluvialis* contains a monoester of 3S,3S'-isomer having one fatty acid combined therewith in a large amount (Renstrom, B., Liaaen-Jensen, S.: Fatty acids of some esterified carotenols, Comp. Biochem. Physiol. B, Comp. Biochem., 1981, 69, p. 625-627.)

Moreover, astaxanthin obtained from *Phaffia Phodozyma* is 3R,3R'-isomer (Andrewes, A. G., Starr, M. P.: (3R,3'R)-Astaxanthin from the yeast *Phaffa rhodozyma*, Phytochem., 1976, 15, p. 1009-1011.), which has a structure reverse to 3S,3S'-isomer that is usually found in the nature. Furthermore, the former one is present in a free form which does not form an ester with a fatty acid (Andrewes, A. G., Phaffia, H. J., Starr, M. P.: Carotenids of *Phaffia rhodozyma*, a red pigmented fermenting yeast, Phytochem., 1976, 15, p. 1003-1007.).

Astaxanthin and an ester thereof are first isolated from lobster (*Astacus gammarus* L.) by R. Kuhn and an assumed structure thereof has been disclosed (Kuhn, R., Soerensen, N. A.: The coloring matters of the lobster (*Astacus gammarus* L.), Z. Angew. Chem., 1938, 51, p. 465-466). Since then, it has been revealed that astaxanthin is widely distributed in the natural world and is usually present as fatty acid esters of astaxanthin and astaxanthin is present also as astaxanthin proteins (ovorubin, clustercyanine) (Cheesman, D. F.: Ovorubin, a chromoprotein from the eggs of the gastropod mollusc *Pomacea canaliculata*, Proc. Roy. Soc. B, 1958, 149, p. 571-587).

The above astaxanthin and an ester thereof (astaxanthins) may be contained as astaxanthin-containing oils separated and extracted from natural products containing astaxanthin and/or an ester thereof. Examples of such astaxanthin-containing oils include extracts from culture products obtained by culturing red yeast *Phaffia*, green alga *Haematococcus*, marine bacteria, and the like and extracts from Antarctic krill.

The *Haematococcus* alga extract (*Haematococcus* alga-derived pigment) is different from the krill-derived pigment and synthesized astaxanthin in view of main ingredients of fatty acid esters (monoester, diester, etc.) (http://www.astaxanthin.co.jp/chemical/basic.html)

The astaxanthins usable in the invention may be the above extracts and products obtained by suitably further purifying the extracts according to need or may be synthetic products. As the above astaxanthins, one extracted from *Haematococcus* algae (also referred to as *Haematococcus* alga extract) is particularly preferred in view of quality and productivity.

As sources of the *Haematococcus* alga extract usable in the invention, there may be specifically mentioned *Haematococcus pluvialis, Haematococcus lacustris, Haematococcus capensis, Haematococcus droebakensis, Haematococcus zimbabwiensis*, and the like.

The method for culturing *Haematococcus* algae usable in the invention is not particularly limited and various methods disclosed in JP-A-8-103288 etc. can be adopted so far as the algae may be changed in morphology from vegetative cells to cyst cells.

The *Haematococcus* alga extract usable in the invention can be obtained by crushing cell walls of the above raw material by the method disclosed in JP-A-5-68585 or the like according to need and extracting the material with adding an organic solvent such as acetone, ether, chloroform, or an alcohol (ethanol, methanol, etc.) or an extraction solvent such as carbon dioxide in a supercritical state.

Moreover, in the invention, commercially available *Haematococcus* alga extracts can be widely employed and there may be mentioned ASTOTS-S, ASTOTS-2.5 O, ASTOTS-5 O, ASTOTS-10 O, and the like manufactured by Takedashiki Co., Ltd., AstaREAL oil 50F, AstaREAL oil 5F, and the like manufactured by Fuji Chemical Industry Co., Ltd., and Bio-Astin SCE7 and the like manufactured by Toyo Koso Kagaku Co., Ltd.

The content of astaxanthins as pure pigment ingredients in the *Haematococcus* alga extract usable in the invention is preferably 0.001 to 50% by mass, more preferably 0.01 to 25% by mass. (In this specification, mass ratio is equal to weight ratio.)

In this connection, the *Haematococcus* alga extract usable in the invention contains, similar to pigments described in JP-A-2-49091, astaxanthin or ester(s) thereof as pure pigment ingredient(s) and generally contains the ester(s) in an amount of 50% by mol or more, preferably 75% by mol or more, more preferably 90% by mol or more.

More detail explanation is described in "Astaxanthin no Kagaku", 2005, Internet <URL: http://www.astaxanthin.co.jp/chemical/basic.htm>.

As these astaxanthins, those extracted with supercritical carbon dioxide are more preferred in view of odor when transformed into a powder.

Fat-Soluble Vitamins

As the fat-soluble vitamins in the invention, there may be mentioned fat-soluble vitamin E's, retinoids, vitamin D's, and oil-soluble derivatives of ascorbic acid and erythorbic acid. Of these, preferred are fat-soluble vitamin E's which are high in antioxidation activity and usable as a radical scavenger.

The fat-soluble vitamin E's are not particularly limited and include tocopherol and tocotrienol and derivatives thereof. There may be mentioned tocopherol and derivatives thereof such as dl-α-tocopherol, dl-β-tocopherol, dl-γ-tocopherol, dl-δ-tocopherol, dl-α-tocopherol acetate, dl-α-tocopherol nicotinate, dl-α-tocopherol linoleate, and dl-α-tocopherol succinate; α-tocotrienol, β-tocotrienol, γ-tocotrienol, δ-tocotrienol, and the like. They may be used singly or a plurality thereof may be used in combination but they may be preferably used as a mixture. The mixture includes those called extracted tocopherol, mixed tocopherol, and the like.

As the retinoids, there may be mentioned vitamin A's such as retinol, 3-hydroxyretinol, retinal, 3-hydroxyretinal, retinoic acid, 3-dihydroretinoic acid, vitamin A acetate; provitamin A's including carotinoids such as α,β,γ-carotenes, β-cryptoxanthin, and echinenone and xanthophyll. As the vitamin D's, there may be mentioned vitamin D's such as vitamins D2 to D7.

Moreover, as the other fat-soluble vitamin substances, esters such as vitamin E nicotinate; vitamin K's such as vitamins K1 to K3.

As the oil-soluble derivatives of ascorbic acid and erythorbic acid, there may be mentioned fatty acid esters of vitamin C such as L-ascorbyl stearate ester, L-ascorbyl tetraisopalmitate ester, L-ascorbyl palmitate ester, erythorbyl palmitate ester, erythorbyl tetraisopalmitate ester, and ascorbyl dioleate; fatty acid esters of vitamin B6 such as pyridoxine dipalmitate, pyridoxine tripalmitate, pyridoxine dilaurate, and pyridoxine dioctanoate; and the like.

Fat-soluble Vitamin-like Substances

The vitamin-like substances are general names of substances which can be synthesized in the body and act as vitamins, and fat-soluble ones are pointed out in particular.

As the fat-soluble vitamin-like substances, there may be mentioned, for example, ubiquinones and ω-3 oils and fats (oils and fats including EPA, DHA, and linoleic acid).

Ubiquinones

As the ubiquinones, coenzyme Q's such as coenzyme Q10 (ubidecarenone) and the like may be mentioned. Coenzyme Q10 was approved and marketed as an ethical drug of metabolic cardiac in 1974 in Japan. Thereafter, it has been dealt as a pharmaceutical including OTC. On the other hand, demand thereof has increased as a health-food material with high effectiveness and safety for these 10 years in foreign countries (mainly Europe and the United States). Also in Japan, coenzyme Q10 was cited on a list of "essential ingredients (raw materials) to be approved as foods unless medical effect and efficacy are not advocated" in Notification of Director of Pharmaceutical Bureau of Ministry of Health, Labour and Welfare in 2001 of "Amendment of Criteria for Scope of Pharmaceuticals" (No. 243 from Pharmaceutical Bureau) and thus, there was made deregulation that it might be dealt as a food. In Japan, a variety of functions of the food material have attracted attention and a large number of general foods (so-called health foods) containing coenzyme Q10 have been put into commercialization.

For utilizing the functions of coenzyme Q10, it is important to make the fat-soluble material water-soluble. Since it is considered that the fat-soluble property is accompanied by low absorbability in the living body unless the substance is ingested together with foods, the purpose of making it water-soluble is to obtain secure absorbability in the living body even if the substance is ingested any time and anywhere in order to improve such a disadvantage. They may be used singly or a plurality thereof may be used in combination.

ω-3 Oils and Fats

As the ω-3 oils and fats, there may be mentioned linoleic acid, eicosapentaenoic acid (EPA), and docosahexaenoic acid (DHA) as well as fish oils containing them.

The oil-soluble antioxidant substance powder may contain the other oily ingredient(s). As compound usable as the oily ingredients, there may be mentioned liquid oils and fats (fat oils) and solid oils and fats (fats) at ordinary temperature.

Examples of the above liquid oils and fats include olive oil, camellia oil, *macadamia* nut oil, castor oil, avocado oil, evening primrose oil, turtle oil, corn oil, mink oil, rape seed oil, egg yolk oil, sesame oil, persic oil, wheat germ oil, camellia sasanqua oil, linseed oil, safflower oil, cotton seed oil, *perilla* oil, soybean oil, peanut oil, tea seed oil, kaya oil, rice bran oil, Chinese tung oil, Japanese tung oil, jojoba oil, germ oil, triglycerin, glycerin trioctanoate, glycerin triisopalmitate, salad oil, safflower oil, palm oil, coconut oil, peanut oil, almond oil, hazelnut oil, walnut oil, grape seed oil, squalen, squalan, and the like.

Moreover, as the above solid oils and fats, there may be mentioned beef tallow, hardened beef tallow, hoof oil, beef bone oil, mink oil, egg yolk oil, lard, horse tallow, mutton tallow, hardened oil, cacao butter, palm butter, hardened palm butter, palm oil, hardened palm oil, Japan wax, Japan wax kernel oil, hardened castor oil, and the like.

As the other oily ingredient(s), there may be used other ingredients usually used as an ultraviolet absorbent, an anti-inflammatory agent, a moisturizing agent, a hair protecting agent, a dispersant, a solvent, a whitening agent, an antiblotch agent, a cell-activating agent, an emollient, a keratolytic agent, an antistatic agent, vitamins, a metabolic syndrome remedial agent, an antihypertensive agent, a sedative agent, and the like. Examples thereof include hydrocarbons such as liquid paraffin, paraffin, Vaseline, ceresin, and microcrystalline wax; waxes such as carnauba wax, candelilla wax, jojoba oil, yellow beeswax, and lanolin; esters such as isopropyl myristate, 2-octyldodecyl myristate, cetyl 2-ethylhexanoate, and diisostearyl malate; fatty acids such as palmitic acid, stearic acid, isostearic acid, linoleic acid, and arachidonic acid; higher alcohols such as cetyl alcohol, stearyl alcohol, isostearyl alcohol, and 2-octyldodecanol; silicone oils such as methylpolysiloxane and methylphenylpolysiloxane; and also polymers, oil-soluble pigments, oil-soluble proteins, and the like. Moreover, various plant-derived oils and animal-derived oils which are mixtures thereof may be also included.

In order to increase dispersibility into water, the above oily ingredients are preferably used in combination of two or more thereof. As the oily ingredient usable in combination for the purpose, DHA, squalen, or squalan is preferred and squalan is particularly preferred. Particularly, in the case of an oily ingredient like coenzyme Q10 which is solid at room temperature, it is particularly preferred to use DHA, squalen, squalan, or the like in combination.

The content of the oil-soluble antioxidant substance in the oil-soluble antioxidant substance powder is preferably 0.1 to 15% by mass, more preferably 0.5 to 10% by mass, and further preferably 0.2 to 6% by mass.

Since the content of the oil-soluble antioxidant substance is 0.1% by mass or more as described above, it is a sufficient amount for obtaining an effect by the oil-soluble antioxidant substance without using a large amount thereof. On the other hand, by controlling the amount to less than 15% by mass, exudation of the oil-soluble antioxidant substance onto the powder surface with time during storage is effectively suppressed and it becomes possible to improve handling ability, so that individual cases are preferred.

In the invention, in the case where the other oily ingredient(s) is used in combination with the above oil-soluble antioxidant substance, the oil-soluble antioxidant substance can be used in an amount of preferably 10% by mass to 99% by mass, more preferably 50% by mass to 99% by mass based on the total amount of the oily ingredients.

In the invention, the oil-soluble antioxidant substance is preferably a powder composition obtained by drying an emulsion composition containing (a) a sucrose fatty acid ester and/or a polyglycerin fatty acid ester and (b) a phospholipid and mass composition ratios of (a) and (b) are the same or the ratio of (a) is larger than the ratio of (b). In particular, when such a powder composition is formed in the case of using carotinoids, fat-soluble vitamins, ubiquinones, ω-3 oils and fats, particularly carotinoids (also called carotenoids) which are oil-soluble functional pigments among the oil-soluble antioxidant substances, there can be obtained a powder composition having remarkable effects of high transparency at the time when dispersed in water and excellent stability during storage.

(a) Sucrose Fatty Acid Ester and/or Polyglycerin Fatty Acid Ester

The oil-soluble antioxidant substance powder of the invention preferably contains a sucrose fatty acid ester and/or a polyglycerin fatty acid ester.

They both act as surfactants and also average particle size can be made smaller when an emulsion composition is formed.

With regard to the sucrose fatty acid ester, the fatty acid preferably has 12 or more carbon atoms, more preferably 12 to 20 carbon atoms from the viewpoint of surface activity. By using a fatty acid having 12 or more carbon atoms, there is a case where emulsion particles having a smaller average particle size can be formed.

As the sucrose fatty acid ester, there may be mentioned sucrose dioleic acid ester, sucrose distearic acid ester, sucrose dipalmitic acid ester, sucrose dimyristic acid ester, sucrose dilauric acid ester, sucrose monooleic acid ester, sucrose monostearic acid ester, sucrose monopalmitic acid ester, sucrose monomyristic acid ester, sucrose monolauric acid ester, and the like. Of these, a sucrose monoester is preferred and particularly, sucrose monolauric acid ester or sucrose monooleic acid ester is more preferred. In the invention, these sucrose fatty acid esters can be used singly or as a mixture.

Examples of commercially available products include RYOTO Sugar Esters S-070, S-170, S-270, S-370, S-370F, S-570, S-770, S-970, S-1170, S-1170F, S-1570, S-1670, P-0700, P-170, P-1570, P-1670, M-1695, O-170, O-1570, OWA-1570, L-195, L-595, L-1695, LWA-1570, B-370, B-370F, ER-190, and POS-135 manufactured by Mitsubishi-kagaku Food Corporation; DK esters SS, F160, F140, F110, F90, F70, F50, F-A50, F-20W, F-10, F-A10E, Cosmelike B-30, S-10, S-50, S-70, S-110, S-160, S-190, SA-10, SA-50, P-10, P-160, M-160, L-10, L-50, L-160, L-150A, L-160A, R-10, R-20, O-10, and O-150 manufactured by Daiich Kogyo Seiyaku Co., Ltd.; and the like.

As the polyglycerin fatty acid ester for use in the invention, there may be mentioned esters of polyglycerins having an average polymerization degree of 2 or more, preferably 6 to 15, more preferably 8 to 10 with fatty acids having 8 to 18 carbon atoms, such as caprylic acid, capric acid, lauric acid, myristic acid, palmitic acid, stearic acid, oleic acid, and linoleic acid. Preferable examples of the polyglycerin fatty acid ester include hexaglycerin monooleic acid ester, hexaglycerin monostearic acid ester, hexaglycerin monopalmitic acid ester, hexaglycerin monomyristic acid ester, hexaglycerin monolauric acid ester, decaglycerin monooleic acid ester, decaglycerin monostearic acid ester, decaglycerin monopalmitic acid ester, decaglycerin monomyristic acid ester, decaglycerin monolauric acid ester, and the like.

Of these, more preferred are decaglycerin monooleic acid ester (HLB=12), decaglycerin monostearic acid ester (HLB=12), decaglycerin monopalmitic acid ester (HLB=13), decaglycerin monomyristic acid ester (HLB=14), decaglycerin monolauric acid ester (HLB=16), and the like.

These polyglycerin fatty acid esters can be used singly or as a mixture.

Examples of commercially available products include NIKKOL DGMS, NIKKOL DGMO-CV, NIKKOL DGMO-90V, NIKKOL DGDO, NIKKOL DGMIS, NIKKOL DGTIS, NIKKOL Tetraglyn 1-SV, NIKKOL Tetraglyn 1-O, NIKKOL Tetraglyn 3-S, NIKKOL Tetraglyn 5-S, NIKKOL Tetraglyn 5-O, NIKKOL Hexaglyn 1-L, NIKKOL Hexaglyn 1-M, NIKKOL Hexaglyn 1-SV, NIKKOL Hexaglyn 1-O, NIKKOL Hexaglyn 3-S, NIKKOL Hexaglyn 4-B, NIKKOL Hexaglyn 5-S, NIKKOL Hexaglyn 5-O, NIKKOL Hexaglyn PR-15, NIKKOL Decaglyn 1-L, NIKKOL Decaglyn 1-M, NIKKOL Decaglyn 1-SV, NIKKOL Decaglyn 1-50SV, NIKKOL Decaglyn 1-ISV, NIKKOL Decaglyn 1-O, NIKKOL Decaglyn 1-OV, NIKKOL Decaglyn 1-LN, NIKKOL Decaglyn 2-SV, NIKKOL Decaglyn 2-ISV, NIKKOL Decaglyn 3-SV, NIKKOL Decaglyn 3-OV, NIKKOL Decaglyn 5-SV, NIKKOL Decaglyn 5-HS, NIKKOL Decaglyn 5-IS, NIKKOL Decaglyn 5-OV, NIKKOL Decaglyn 5-O—R, NIKKOL Decaglyn 7-S, NIKKOL Decaglyn 7-O, NIKKOL Decaglyn 10-SV, NIKKOL Decaglyn 10-IS, NIKKOL Decaglyn 10-OV, NIKKOL Decaglyn 10-MAC, and NIKKOL Decaglyn PR-20 manufactured by Nikko Chemicals Co., Ltd.; RYOTO Polygly Esters L-7D, L-10D, M-10D, P-8D, SWA-10D, SWA-15D, SWA-20D, S-24D, S-28D, 0-15D, 0-50D, B-70D, B-100D, ER-60D, LOP-120DP, DS13W, DS3, HS11, HS9, TS4, TS2, DL15, and DO13 manufactured by Mitsubishi-kagaku Food Corporation; Sunsoft Q-17UL, Sunsoft Q-14S, Sunsoft A-141C manufactured by Taiyo Kagaku Co., Ltd.; Poem DO-100 and Poem J-0021 manufactured by Riken Vitamin Co., Ltd.; and the like.

The above (a) ingredient is preferably contained in an amount of preferably 1% by mass to 50% by mass, more preferably 5% by mass to 50% by mass based on the whole oil-soluble antioxidant substance powder in view of emulsification stability and storage stability after re-dissolution and furthermore, the amount can be suitably adjusted within the range according to the intended purpose of the oil-soluble antioxidant substance powder. Particularly, in view of body absorbability, a higher ratio of the (a) ingredient based on the whole oil-soluble antioxidant substance powder within the above range is more preferred. On the other hand, in view of fine particle formation of the emulsion particles at re-dissolution, a lower ratio of the (a) ingredient based on the whole power within the above range is more preferred. For example, in view of fine particle formation at re-dissolution, the (a) ingredient can be in a ratio of preferably 45% by mass or less, more preferably 40% by mass or less based on the oil-soluble antioxidant substance powder. On the other hand, for example, in the case of forming an oil-soluble antioxidant substance powder exhibiting a good body absorbability, the (a) ingredient can be in a ratio of preferably 30% by mass or more, more preferably 40% by mass or more based on the oil-soluble antioxidant substance powder.

In the oil-soluble antioxidant substance powder of the invention, either of these sucrose fatty acid ester and polyglycerin fatty acid ester may be contained and, in view of further improving the storage stability of the powder, they are preferably used in combination. In the case where the sucrose fatty acid ester and polyglycerin fatty acid ester are used in combination as the (a) ingredient, the ratio is not particularly limited but, in view of improving the storage stability of the powder, the mass ratio of the sucrose fatty acid ester and polyglycerin fatty acid ester is preferably 10:90 to 90:10, more preferably 20:80 to 80:20.

As these sucrose fatty acid ester and polyglycerin fatty acid ester, preferred are those having HLB of 8 or more, more preferred are those having HLB of 10 or more, and particularly preferred are those having HLB of 12 or more. The upper limit of the HLB value is not particularly limited but is generally 18 or less, preferably 17 or less.

The HLB is a hydrophilic-hydrophobic balance usually used in the field of surfactants and any calculation equations, for example, the Kawakami equation or the like can be used. In the invention, the following Kawakami equation is adopted.

$$HLB = 7 + 11.7 \log(M_W/M_O)$$

wherein $M_W$ is molecular weight of a hydrophilic group and $M_O$ is molecular weight of a hydrophobic group.

Moreover, the numerical values of HLB described in catalogs or the like may be employed.

Furthermore, as is apparent from the above equation, a surfactant having any HLB value can be obtained utilizing the additive property of HLB.

The oil-soluble antioxidant substance powder of the invention may contain a surfactant mentioned in the following other than the above (a) ingredient and the (b) ingredient to be described below. As the surfactant in the invention, a nonionic surfactant (hydrophilic surfactant) which dissolves in an aqueous medium can remarkably reduce surface tension of oil phase/water phase in an emulsion composition and, as a result, the particle size can be decreased, so that the surfactant is preferred.

Examples of the nonionic surfactant usable in the invention include glycerin fatty acid esters, organic acid monoglycerides, propylene glycol fatty acid esters, polyglycerin-condensed ricinoleic acid esters, sorbitan fatty acid esters, and polyoxyethylene sorbitan fatty acid esters, and the like. More preferred are sorbitan fatty acid esters and polyoxyethylene-sorbitan fatty acid esters. Moreover, the above surfactants are not necessarily highly purified ones and may be reaction mixtures.

The sorbitan fatty acid esters for use in the invention are those derived from fatty acids having preferably 8 or more carbon atoms, more preferably 12 or more carbon atoms. Preferable examples of the sorbitan fatty acid esters include sorbitan monocaprylate, sorbitan monolaurate, sorbitan monostearate, sorbitan sesquistearic acid, sorbitan tristearate, sorbitan isostearate, sorbitan sesquiisostearate, sorbitan oleate, sorbitan sesquioleate, sorbitan trioleate, and the like.

These sorbitan fatty acid esters can be used singly or as a mixture.

Examples of commercially available products include NIKKOL SL-10, SP-10V, SS-10V, SS-10MV, SS-15V, SS-30V, SI-10RV, SI-15RV, SO-10V, SO-15MV, SO-15V, SO-30V, SO-10R, SO-15R, SO-30R, and SO-15EX manufactured by Nikko Chemicals, Co., Ltd.; Solgen 30V, 40V, 50V, 90, and 110 manufactured by Daiichi Kogyo Seiyaku, Co., Ltd.; Reodol AS-10V, AO-10V, AO-15V, SP-L10, SP-P10, SP-S10V, SP-S30V, SP-O10V, and SP-O30V manufactured by Kao Corporation; and the like.

The polyoxyethylene sorbitan fatty acid esters for use in the invention are those derived from fatty acids having preferably 8 or more carbon atoms, more preferably 12 or more carbon atoms. Moreover, the length (added mol number) of the ethylene oxides of the polyoxyethylene is preferably 2 to 100, more preferably 4 to 50.

Preferable examples of the polyoxyethylene sorbitan fatty acid esters include polyoxyethylene sorbitan monocaprylate, polyoxyethylene sorbitan monolaurate, polyoxyethylene sorbitan monostearate, polyoxyethylene sorbitan sesquistearic acid, polyoxyethylene sorbitan tristearate, polyoxyethylene sorbitan isostearate, polyoxyethylene sorbitan sesquiisostearate, polyoxyethylene sorbitan oleate, polyoxyethylene sorbitan sesquioleate, polyoxyethylene sorbitan trioleate, and the like.

These polyoxyethylene sorbitan fatty acid esters can be used singly or as a mixture.

Examples of commercially available products include NIKKOL TL-10, NIKKOL TP-10V, NIKKOL TS-10V, NIKKOL TS-10MV, NIKKOL TS-106V, NIKKOL TS-30V, NIKKOL TI-10V, NIKKOL TO-10V, NIKKOL TO-10MV, NIKKOL TO-106V, and NIKKOL TO-30V manufactured by Nikko Chemicals, Co., Ltd.; Rheodol TW-L106, TW-L120, TW-P120, TW-S106V, TW-S120V, TW-S320V, TW-0106V, TW-0120V, TW-0320V, and TW-IS399C and Rheodol Super SP-L10 and TW-L120 manufactured by Kao Corporation; Sorgen TW-20, TW-60V, and TW-80V manufactured by Daiichi Seiyaku Kogyo, Co., Ltd. and the like.

The amount of these other surfactants is preferably 5.0 equivalent or less, more preferably 2 equivalents or less, further preferably 1.5 equivalents or less, particularly preferably 1 equivalent or less to the amount of the oil-soluble antioxidant substance in order to easily obtain an emulsion having fine particle size. By controlling the amount of the above surfactant to 2 equivalents or less, a problem of severe foaming and the like tends to disappear and thus the case is preferred.

The amount of these optional surfactants to be added is preferably 0.01 to 30% by mass, more preferably 0.1 to 20% by mass, and further preferably 1 to 15% by mass.

By controlling the amount of the above surfactant to 0.01% by mass or more, the surface tension between oil phase/water phase is easily decreased at the time when an emulsion composition is formed. Moreover, by controlling the amount to 30% by mass or less, the problem of severe foaming of the emulsion composition hardly occurs without use of an excess amount. Thus, the cases are preferred.

(b) Phospholipid

The oil-soluble antioxidant substance powder of the invention contains a phospholipid as the (b) ingredient.

The phospholipids herein means glycerophospholipids containing no glycerin and sphingophospholipids containing sphingosine, which are, among complex lipids, esters composed of a fatty acid, an alcohol, phosphoric acid, and a nitrogen compound and belong to a group of compounds having a phosphoric acid ester and a fatty acid ester.

Examples of the glycerophospholipids usable in the invention include ingredients such as phosphatidic acid, bisphosphatidic acid, lecithin (phosphatidylcholine), phosphatidylethanolamine, phosphatidylmethylethanolamine, phosphatidylserine, phosphatidylinositol, phosphatidylglycerin, and diphosphatidylglycerin (cardiolipin), as well as those derived from plants such as soy bean, corn, peanut, rape seed, wheat, and the like containing these ingredients and various lecithins derived from animals such as egg yolk and cattle and derived from microorganisms such as *Escherichia coli*.

As the sphingophospholipid usable in the invention, for example, sphingomyelin may be mentioned.

Additionally, in the invention, as the glycerophospholipid, a glycerophospholipid having one aliphatic acid residue in one molecule as a result of hydrolysis, i.e., lysolecithin is also included.

Such a lysolecithin is obtained by hydrolysis of lecithin with an acid or an alkali catalyst but can be also obtained by hydrolysis of lecithin with phospholipase A1 or A2.

As such lysolecithin, there may be mentioned lysophosphatidic acid, lysophosphatidylglycerin, lysophosphatidylinositol, lysophosphatidylethanolamine, lysophosphatidylmethylethanolamine, lysophosphatidylcholine (lysolecithin), lysophosphatidylserine, and the like.

Furthermore, as the glycerophospholipid represented by the above lecithin, hydrogenated or hydroxylated one can be also used in the invention.

The above hydrogenation is carried out, for example, by reacting lecithin with hydrogen in the presence of a catalyst, thereby an unsaturated bond of the fatty acid part being hydrogenated. By hydrogenation, oxidation stability of lecithin is enhanced.

Moreover, the above hydroxylation is carried out by heating lecithin together with a highly concentrated hydrogen peroxide and an organic acid such as acetic acid, tartaric acid, or butyric acid, thereby an unsaturated bond of the fatty acid part being hydroxylated. By hydroxylation, hydrophilicity of lecithin is improved.

Among the above (b) phospholipids, in view of storage stability of the powder, preferred is one having two fatty acid residues in one molecule and particularly preferred is lecithin.

Since the lecithin has a hydrophilic group and a hydrophobic group in the molecule, it has been widely used as an emulsifier in the fields of foods, pharmaceuticals, and cosmetics.

Moreover, hydrogenated or hydroxylated lecithin is particularly preferred for the application to cosmetic uses.

Lecithin having a purity of 60% by mass or more is industrially utilized as lecithin. However, in the invention, lecithin having a purity of 80% by mass or more, generally called "highly pure lecithin" is preferred and more preferred is one having a purity of 90% by mass or more.

The purity of lecithin (% by mass) is determined by subtracting the weights of toluene-insoluble matter and acetone-soluble matter with utilization of properties that lecithin is easily soluble in toluene and is not soluble in acetone. The highly pure lecithin has higher lipophilicity as compared with lysolecithin. Therefore, compatibility of lecithin with the oil-soluble antioxidant substance increases and emulsion stability can be enhanced, so that the lecithin is preferred.

The phospholipids for use in the invention can be used singly or in the form of mixture of two or more thereof.

In the oil-soluble antioxidant substance powder in the invention, the content of the phospholipid is preferably from 0.1 to 10% by mass, more preferably 0.2 to 5% by mass, and further preferably 0.5 to 2% by mass based on the whole oil-soluble antioxidant substance powder.

By controlling the content of the above phospholipid to 0.1% by mass or more, the emulsification stability of the emulsion composition tends to be good. Moreover, by controlling the above content to 10% by mass or less, an excessive phospholipid does not form a phospholipid dispersion in water apart from the oil-soluble antioxidant substance and thus the case is preferred in view of emulsification stability of the emulsion composition.

In the oil-soluble antioxidant substance powder, the composition ratios of (a) and (b) are the same or the ratio of the (a) ingredient is larger. Since the (a) ingredient is present in the oil-soluble antioxidant substance powder in an amount the same as or larger than the amount of the (b) ingredient, fine particle size can be obtained and also storage stability of the particle size and storage stability of the emulsion can be made satisfactory.

With regard to the composition ratios of the (a) ingredient and the (b) ingredient, in view of suitable amount for fine particle formation and emulsion stability and in view of regulation of foaming at the time when an emulsion composition is formed, the (a) ingredient is preferably 1 time to 100 times, more preferably more than 5 times to 80 times the (b) ingredient.

(d) Excipient

The oil-soluble antioxidant substance powder preferably contains an excipient as the (d) ingredient in view of easiness of powder formation.

The excipient may be any water-soluble substance generally used for stable particle formation of the oil-soluble antioxidant substance in the oil-soluble antioxidant substance powder and there may be mentioned monosaccharides and polysaccharides such as glucose, fruit sugar, lactose, malt sugar, sucrose, dextrin, maltodextrin, cyclodextrin, maltose, fructose, inulin, and trehalose; sugar alcohols such as sorbitol, mannitol, maltitol, lactose, maltothreitol, and xylitol; inorganic salts such as sodium chloride and sodium sulfate; thickened polysaccharides such as gum arabic, guar gum, pectin, pullulan, and sodium alginate; cellulose derivatives such as methyl cellulose and carboxymethyl cellulose sodium; starch derivatives obtained by subjecting starch to esterification, etherification treatment, or terminal reduction treatment; and also processed starch, gelatin decomposates, agar, polyvinyl alcohol, and the like. Among them, in view of solubility, preferred are monosaccharides, polysaccharrides, sugar alcohols, and inorganic salts. In view of moisture-absorbing properties and particle-forming properties, gum arabic, inulin, and dextrin are particularly preferred, and inulin is most preferred. They can be used singly or in combination of two or more thereof.

These excipients are used preferably 20% by mass to 95% by mss, more preferably 30% by mass to 85% by mass based on the whole oil-soluble antioxidant substance powder in view of efficiently and satisfactorily holding the oil-soluble antioxidant substance.

If necessary, to the oil-soluble antioxidant substance powder can suitably added the other additive(s). In view of easiness of powder formation, it is preferable to contain no polyhydric alcohol which is liquid at ordinary temperature. The polyhydric alcohol herein means an alcohol having two or more hydric valencies and examples thereof include glycerin, diglycerin, triglycerin, polyglycerin, 3-methyl-1,3-butanediol, 1,3-butylene glycol, isoprene glycol, 1,2-pentanediol, 1,2-hexanediol, propylene glycol, dipropylene glycol, polypropylene glycol, ethylene glycol, diethylene glycol, pentaerythritol, neopentyl glycol, and the like. They can be used singly or as a mixture of two or more thereof.

In the invention, the phrase "to contain no polyhydric alcohol which is liquid at ordinary temperature" means 1% by mass or less based on the whole oil-soluble antioxidant substance powder and is preferably 0.5% by mass or less, more preferably 0.1% by mass, and most preferably 0% by mass.

The oil-soluble antioxidant substance powder is preferably obtained by preparing an emulsion composition containing the (a) ingredient and the (b) ingredient described above and drying the composition.

Namely, the oil-soluble antioxidant substance powder can be obtained by a production process comprising a step of producing an emulsion composition wherein (a) a sucrose fatty acid ester and/or a polyglycerin fatty acid ester and (b) a phospholipid are contained and the mass composition ratios of (a) and (b) are the same or the ratio of (a) is larger than the ratio of (b) and a step of drying the resulting emulsion composition.

<Production Process of Emulsion Composition>

The production process of the emulsion composition is not particularly limited and is preferably a production process comprising, for example, I) a step of dissolving a surfactant in an aqueous medium (water or the like) to obtain a water phase, II) a step of mixing and dissolving the above oil-soluble antioxidant substance and phospholipid to obtain an oil phase, and III) a step of mixing the water phase and the oil phase under stirring and effecting emulsion dispersion to obtain an emulsion composition.

The ingredients contained in the oil phase and water phase in the above production process are the same as the aforementioned compositional ingredients of the oil-soluble antioxidant substance powder, preferable examples and preferable amounts are also the same, and preferable combinations are more preferred.

The ratio (mass) of the oil phase to the water phase in the above emulsification dispersion is not particularly limited but, in general, a smaller ratio of the oil phase/water phase results in smaller particle size. However, when the ratio of the oil phase/water phase is too small, there arises a practical problem since the content of the active ingredient decreases and also emulsion stability of the emulsion composition becomes worse in some cases since the surfactant concentration decreases.

From the above viewpoints, the ratio of oil phase/water phase (% by mass) is preferably 0.1/99.9 to 50/50, more preferably 0.5/99.5 to 30/70, and further preferably 1/99 to 20/80.

On this occasion, the ratio of water in the emulsion composition is preferably 80% by mass, more preferably 85% by mass in view of formation of fine emulsion particles.

The above emulsification dispersion may be effected by one-step emulsification operation but emulsification operation comprising two or more steps is preferred in view of obtaining homogeneous fine emulsified particles.

Specifically, it is particularly preferred to use two or more kinds of emulsification apparatus by performing a method of emulsification passing through a high-pressure homogenizer or the like in addition to the one-step emulsification operation wherein emulsification is performed using an ordinary apparatus utilizing shearing action (e.g., a stirrer, an impeller stirrer, a homomixer, a continuous flow shearing apparatus, etc.). By the use of the high-pressure homogenizer, the emulsion can be made more homogeneous, which contains homogeneous liquid drops of fine particles. Moreover, the emulsification may be performed two or more times for the purpose of forming liquid drops having more homogeneous particle size.

The temperature conditions at the emulsification dispersion in the invention is not particularly limited but is preferably 10 to 100° C. from the viewpoint of stability of the oil-soluble antioxidant substance. Depending on the melting point of the oil-soluble antioxidant substance to be handled, a preferable range can be suitably selected.

As the above high-pressure homogenizer, there may be mentioned a chamber-type high-pressure homogenizer having a chamber wherein a flow path of a liquid to be treated is fixed and a homogeneous valve-type high-pressure homogenizer having a homogeneous valve. Of these, the homogeneous valve-type high-pressure homogenizer is particularly preferred for the production process of the emulsion composition according to the invention owing to its wide operation range since the width of the flow path of the liquid to be treated can be easily controlled and pressure and flow rate at the operation can be arbitrarily set.

Moreover, since a mechanism for increasing pressure is easy to manufacture, the chamber-type high-pressure homogenizer is also suitably used in the case where ultrahigh pressure is required although freedom of operation is low.

As the above chamber-type high-pressure homogenizer, there may be mentioned a microfluidizer (manufactured by Microfluidics Company), a nanomizer (manufactured by Furuta Kikai Kogyo K.K.), an ultimizer (manufactured by Sugino Machine Limited), and the like.

As the above homogeneous valve-type high-pressure homogenizer, there may be mentioned a Gorlin-type homogenizer (manufactured by APV Company), a Lannier-type homogenizer (manufactured by Lannier Company), a high-pressure homogenizer (manufactured by Niro Soavi Company), a homogenizer (manufactured by Sanwa Engineering Ltd.), a high-pressure homogenizer (manufactured by Izumi Food Machinery Co., Ltd.), an ultrahigh pressure homogenizer (manufactured by Ika Company), and the like.

In the invention, the pressure of the above homogenizer at treatment is preferably 50 MPa or more, more preferably 50 to 250 MPa, and further preferably 100 to 250 MPa.

Moreover, the emulsion that is an emulsified and dispersed composition is preferably cooled through some cooling device within 30 seconds, preferably 3 seconds immediately after the passage through the chamber from the viewpoint of maintaining the particle size of the dispersed particles.

The emulsion composition obtained by such a step is an O/W emulsion where emulsified particles containing the oil-soluble antioxidant substance is dispersed in an aqueous medium.

Particularly, in the invention, an emulsion composition where fine emulsion particles are homogeneously dispersed can be obtained.

The particle size of the emulsion composition obtained is preferably 200 nm or less in view of particle stability and transparency and, in view of transparency, more preferably 130 nm or less, most preferably 90 nm or less.

In the invention, the particle size of the emulsion composition can be measured by means of a commercially available particle-size distribution meter or the like. As the size distribution measuring method of the emulsion, there are known an optical microscope method, a confocal laser scanning microscope method, an electron microscope method, an atomic force microscope method, a static light-scattering method, a laser diffraction method, a dynamic light-scattering method, a centrifugal sedimentation method, an electrical pulse measuring method, a chromatography method, an ultrasonic attenuating method, and the like and an apparatus corresponding to each principle is commercially available.

Because of particle size range in the invention and easiness of measurement, the dynamic light-scattering method is preferred at the emulsion particle size measurement in the invention. As commercially available measuring apparatus using the dynamic light-scattering method, there may be mentioned a nanotrac UPA (Nikkiso Co., Ltd.), a dynamic light scattering particle size analyzer LB-550 (Horiba Ltd.), a fiber-optics particle analyzer FPAR-1000 (Otsuka Electronics Co., Ltd.), and the like.

In the measuring method of particle size in the invention, for example, in the case of the fiber-optics particle analyzer FPAR-1000 (Otsuka Electronics Co., Ltd.), a 10% by mass aqueous solution is prepared and is subjected to measurement under standard measuring conditions of the apparatus in the case of an emulsion composition. On the other hand, in the case of the oil-soluble antioxidant substance powder, a 1% by mass aqueous solution is prepared and is subjected to measurement under the same conditions as in the case of an emulsion composition.

The particle size of the above emulsion composition can be adjusted by factors such as stirring conditions (shear force, temperature, pressure) in the production process and the ratio of oil phase/water phase in addition to the ingredients of the emulsion composition.

The emulsion composition obtained as above is subjected to drying in a drying step.

The drying method applicable to the present production process may be any method so far as it is a method usually used in this application field and there may be mentioned spray drying, freeze drying, vacuum drying, shelf drying, belt drying, drum drying, and the like. Of these, spray drying and freeze drying are preferred in view of handling of a powder.

The oil-soluble antioxidant substance powder thus obtained can constitute an emulsion composition having a good storage stability in particle size, pigment and dispersibility of emulsion particles through re-dissolution of the powder into an aqueous medium which depends on an objective product.

With regard to the particle size in the emulsion composition obtained after re-dissolution, the average particle size may be 200 nm or less in view of transparency and absorbability when formed into a 1% by mass aqueous solution. In view of good transparency and dispersion stability and the above various kinds of storage stability, the particle size is preferably 1 nm or more and less than 130 nm.

(B) Water-Soluble Antioxidant Substance Powder

As the water-soluble antioxidant substance, those used in the fields of foods, pharmaceuticals, and the like can be employed and, for example, there can be used ascorbic acid or derivatives thereof, erythorbic acid or salts thereof, sulfite salts, bisulfite salts, metasulfite salts, plant extracts having antioxidation ability (tea extracts, apple extracts, etc.). A plurality of them may be used.

Among the water-soluble antioxidant substances, vitamin C (ascorbic acid), a catechin and a flavonoid, etc. are preferred.

More preferably, there may be mentioned vitamin C, quercetin, proanthocyanidin, pine bark extracts, anthocyanin, and epigallocatechin gallate.

The water-soluble antioxidant substance is preferably an oil-coated powder. Thereby, a reaction induced by the contact with the other antioxidant substance is prevented and thus such a powder is preferred in view of stability with time.

The water-soluble antioxidant substance is preferably a radical scavenger. The radical scavenger is an additive which plays a role of suppressing generation of radicals and also trapping generated radicals as rapid as possible to discontinue a chain reaction (source reference: "Yukagaku Binran 4th edition", ed. by Japan Oil Chemists' Society, 2001).

As a direct method for confirming the function as the radical scavenger, there is known a method wherein the mode of radical trapping after mixing with a reagent is measured on a spectrophotometer or ESR (electron spin resonance apparatus). In these methods, DPPH (1,1-diphenyl-2-picrylhydrazyl) or carbinoxy radical is used as the reagent.

In the invention, a compound which shows a property that a time required for increasing a peroxide value (POV value) of an oil and fat to 60 meq/kg under the following experimental conditions utilizing autoxidation reaction of the oil and fat is twice the time for blank is defined as the "radical scavenger". The peroxide value (POV value) of an oil and fat is measured in a usual manner.

<Conditions>

Oil and fat: olive oil

Amount of analyte added: 0.1% by mass based on the oil and fat

Test method: A sample is heated at 190° C., the POV value was measured with time in a usual manner, and a time required for reaching 60 meq/kg was calculated.

The radical scavenger in the invention is preferably a radical scavenger showing a property that a time required for reaching the above POV value of 60 meq/kg is 5 times or more the time for blank.

Compounds usable as the radical scavenger in the invention may be any compounds which act as the radical scavenger among various antioxidants described in "Kousankazai no Riron to Jissai" (written by Kajimoto, San Shobo, 1984) and "Sankabousizai Handbook" (written by Saruhashi, Nishino, and Tabata, Taiseisha Ltd., 1976). Specifically, there may be mentioned compounds having phenolic OH, amine-based compounds such as phenylenediamine, oil-soluble derivatives of ascorbic acid and erythorbic acid, and the like.

The following will exemplify preferable radical scavengers but the invention is not limited thereto.

The emulsion composition and high-concentration emulsion of the invention preferably contain, as the radical scavenger, at least two kinds of compounds selected from compound groups: (I) a compound group composed of ascorbic acid or erythorbic acid or salts thereof, or ascorbic acid derivatives or erythorbic acid derivatives or salts thereof, and (II) a compound group composed of polyphenols.

The content of the radical scavenger in the emulsion composition of the invention is generally 0.001 to 5.0% by mass, preferably 0.01 to 3.0% by mass, more preferably 0.1 to 2.0% by mass.

The following will mention specific compound examples of the compound groups (I) and (II), which does not limit compounds usable in the invention.

(I) Ascorbic Acid or Erythorbic Acid or Salts Thereof

As the ascorbic acid or ascorbic acid derivatives or salts thereof, there may be mentioned L-ascorbic acid, Na L-ascorbate, K L-ascorbate, Ca L-ascorbate, L-ascorbic acid phosphoric acid ester, magnesium salt of L-ascorbic acid phosphoric acid ester, L-ascorbic acid sulfuric acid ester, disodium slat of L-ascorbic acid sulfuric acid ester, L-ascorbic acid stearic acid ester, L-ascorbic acid 2-glucoside, L-ascorbic acid palmitic acid ester, L-ascorbyl tetraisopalmitate, and the like. Of these, L-ascorbic acid, Na L-ascorbate, L-ascorbic acid stearic acid ester, L-ascorbic acid 2-glucoside, L-ascorbic acid palmitic acid ester, magnesium salt of L-ascorbic acid phosphoric acid ester, disodium slat of L-ascorbic acid sulfuric acid ester, L-ascorbyl tetraisopalmitate are particularly preferred.

As the erythorbic acid or erythorbic acid derivatives or salts thereof, there may be mentioned erythorbic acid, Na erythorbate, K erythorbate, Ca erythorbate, erythorbic acid phosphoric acid ester, erythorbic acid sulfuric acid ester, erythorbic acid palmitic acid ester, erythorbyl tetraisopalmitate, and the like. Of these, erythorbic acid and Na erythorbate are particularly preferred.

As the radical scavenger belonging to the compound group (I) for use in the invention, generally, commercially available ones can be suitably used. Example thereof include L-ascorbic acid (Takeda Chemical Industries, Ltd., Fuso Chemical Co., Ltd., BASF Japan, Daiich Seiyaku Co., Ltd., etc.), Na L-ascorbate (Takeda Chemical Industries, Ltd., Fuso Chemical Co., Ltd., BASF Japan, Daiich Seiyaku Co., Ltd., etc.), ascorbic acid 2-glucoside (trade name AA-2G: Hayashibara Biochemical Labs., Inc.), Mg L-ascorbate phosphate (trade name ascorbic acid PM "SDK" (Showa Denko K.K.), trade name NIKKOL VC-PMG (Nikko Chemicals Co., Ltd.), trade name SeaMate (Takeda Chemical Industries, Ltd.)), ascorbyl palmitate (DSM Nutrition Japan, Kongo Yakuhin, Merck, etc.), and the like.

(II) Compound Group Composed of Polyphenols

As the compound group composed of polyphenols, there may be mentioned flavonoids (catechin, anthocyanin, flavone, isoflavone, flavane, flavanone, rutin), phenolic acids (chlorogenic acid, ellagic acid, gallic acid, propyl gallate), lignans, curcumins, coumarins, and the like. Moreover, since these compounds are contained in a large amount in the following extracts derived from natural products, they can be utilized in the form of extracts.

Examples thereof include licorice extract, cucumber extract, *Millettia reticulata* extract, gentian (entianae scabrae radix) extract, *Geranium thunbergii* extract, cholesterol and derivatives thereof, hawthorn extract, paeoniae radix extract, ginkgo extract, *Scutellaria baicalensis* (Scutellariae Radix) extract, carrot extract, *Rosa rugosa* (Japanese rose) extract, *Cassia nomame* (Cassia) extract, *Potentilla tormentilla* extract, parsley extract, *Paeonia suffruticosa* Andrews (Moutan Cortex) extract, *Chaenomeles lagenariakoidz* (Japanese quince) extract, *Melissa officinalis* extract, yashajitu (yasha) extract, *Saxifraga stolonifera* extract, rosemary (*Rosmarinus officinalis*) extract, lettuce extract, tea extract (oolong tea, red tea, green tea, etc.), microorganism fermentation products, Momordicae Grosvenori extract, and the like (another names, gelenical names, and the like are described in parenthesis). Among these polyphenols, particularly preferable ones include catechin, rosemary extract, glucosylrutin, ellagic acid, and gallic acid.

As the radical scavenger belonging to the compound group (II) for use in the invention, generally, commercially available ones can be suitably used. Example thereof include ellagic acid (Wako Pure Chemical Industries, Ltd., etc.), rosemary extract (trade name RM-21A, RM-21E: Mitsubishi Kagaku Food Corporation, etc.), catechin (trade name Suncatol W-5, No. 1: Taiyo Chemical Corporation, etc.), Na gallate (trade name Suncatol: Taiyo Chemical Corporation, etc.), rutin/glucosylrutin/enzyme-decomposed rutin (trade name Rutin K-2, P-10: Kiriya Chemical Co., Ltd., trade name αG rutin: Hayashibara Biochemical Labs., Inc., etc.), and the like.

The particle size of the water-soluble antioxidant substance powder is not particularly limited and commercially available ones can be utilized or the powder can be prepared in a usual manner.

(C) Minerals

The powder composition of the invention contains at least one of zinc, selenium, manganese, and copper as a mineral ingredient.

The term "mineral" is a generic name of elements other than four elements of hydrogen, carbon, nitrogen, and oxygen among the elements constituting substances in the field of medical science, nutrition science, and food science. More specifically, there may be mentioned sodium (Na), potassium (K), chlorine (Cl), calcium (Ca), magnesium (Mg), phosphorus (P), and sulfur (S) which are essential for human body and called main minerals, iron (Fe), zinc (Zn), Copper (Cu), and Manganese (Mn) which are called microelements I, and cobalt (Co), chromium (Cr), iodine (I), molybdenum (Mo), and selenium (Se) which are called microelements II. When the mineral ingredients are classified in view of the ingestion amount from human diet, the mineral ingredients whose ingestion amount from daily diet is about 100 mg or more are classified into "main minerals". Moreover, the mineral ingredients whose ingestion amount from daily diet is less than about 100 mg are called "microelements" and the microelements are further classified into "microelements I" whose ingestion amount from daily diet is about 1 mg or more and "microelements II" whose ingestion amount is less than 1 mg (Food Style 21, Vol. 2, No. 9, (1998.9)).

Among these mineral ingredients, in the invention, it is preferred to contain antioxidant minerals such as selenium, zinc, manganese, copper, and iron.

The powder composition of the invention further preferably contains mineral ingredients as mineral yeasts. The mineral yeast is a microorganism (preferably yeast) containing a mineral in the cell.

The microorganism is specifically a microorganism whose body is used at food production and itself served for human eating and whose safety is recognized, including yeasts, fungus imperfectus, fungi such as basidiomycetes, and bacteria. Preferably, the microorganism is an edible yeast, which can be used as a vital cell or a dead cell or in a wet state or dry state. Examples of such yeasts include beer yeast, baker's yeast, wine yeast, sake yeast, alcohol yeast, soy paste/soy source yeast, and the like. For example, it is possible to use a wide range of yeasts belonging to Genera *Saccharomyces, Hansenula, Candida, Torulaspora, Torulopsis, Mycotorula*, and the like. The yeasts are usually used singly but a mixture of a plurality kinds thereof may be used, if necessary.

As the minerals and mineral yeasts, various commercially available products for foods can be employed. Also, the mineral yeasts can be prepared by the method described in JP-A-2000-125811.

(D) Thioctic Acid

It is preferred that the powder composition of the invention further contains thioctic acid.

Thioctic acid is not particularly limited and may be a commonly used synthetic product and an extract derived from natural ingredients.

Thioctic acid may be used as a powder as it is but it is preferred to make it easily dispersible in an aqueous solution by combining it with an emulsifier. As an emulsification method with an emulsifier, the method described in JP-A-2007-16000 can be adopted. The emulsifier is preferably one having HLB (Hydrophilic Lipophilic Balance) of 9 or more, preferably 12 or more, further preferably 14 or more and there may be mentioned synthesized emulsifiers such as polyglycerin fatty acid esters, sucrose fatty acid esters, sodium stearoyllactate, calcium stearoyllactate, polyoxyethylene derivatives, and fatty acid salts; lecithin derivatives obtained by chemical treatment or enzymatic treatment of naturally occurring lecithins, such as zymolytic lecithin, hydrogenated zymolytic lecithin, hydroxylecithin, phosphatidylglycerol, phosphatidic acid, and acetylated lecithin; naturally occurring saponins such as soybean saponin and quillai saponin; and the like. The amount of the emulsifier to be used can be suitably adjusted but, in general, it is used in an amount of 0.1 to 10 times the mass of thioctic acid.

Thioctic acid is preferably used as a cyclodextrin-included one (i.e. cyclodextrin/thioctic acid complex). Thereby, a reaction induced by the contact with the other antioxidant substance is prevented and thus the stability with time is improved.

As a method of inclusion with cyclodextrin, for example, a general method as described in JP-A-2006-169253 can be used.

<Mixing Ratio>

It is further preferred to contain 6 to 70% by mass of the oil-soluble antioxidant substance powder, 10 to 80% by mass of the water-soluble antioxidant substance, and 2 to 60% by mass of thioctic acid based on the total amount of the powder composition.

More preferably, it is further preferred to contain 20 to 50% by mass of the oil-soluble antioxidant substance powder, 20 to 60% by mass of the water-soluble antioxidant substance, and 10 to 50% by mass of thioctic acid based on the total amount of the powder composition.

Moreover, in the case where the powder composition contains an excipient, the excipient is further preferably contained in an amount of 5 to 60% by mass based on the total amount of the powder composition.

<Powder>

It is preferred to contain (A) oil-soluble antioxidant substance powder, (B) water-soluble antioxidant substance powder and (D) thioctic acid individually as separate powders.

The form of the powder composition of the invention to be administered is not particularly limited and, for example, the powder may be ingested as it is as a powder medicine or it may be encapsulated in an oblate or a capsule.

In the case where the antioxidant substance powder of the invention is formulated into a capsule preparation, it may be in the form of hard capsule, soft capsule, microcapsule, or seamless capsule and it is a preferable characteristic that the capsule film is composed of one or more of pig hide gelatin, pig bone gelatin, fish gelatin, or natural hydrophilic polymers. These capsule films can be prepared by any well-known conventional method. The term "to be composed of pig hide gelatin, pig bone gelatin, fish gelatin, or natural hydrophilic polymers" means that the total amount of the pig hide gelatin, pig bone gelatin, fish gelatin, and natural hydrophilic polymers is 30% by weight or more, preferably 40% by weight or more, more preferably 50% by weight or more, and particularly preferably 60% by weight or more based on the total weight of the capsule film. In this connection, the other materials such as cowskin gelatin may be contained in the capsule film unless the advantages of the invention are not impaired.

The natural hydrophilic polymer is a hydrophilic polymer obtained by purification or synthesis from a material derived from a natural animal or plant or a processed polymer thereof. There may be exemplified at least one selected from alginic acid or salts thereof, agar gum, guar gum, locust bean gum, cod gum, ghatti gum, *Khaya grandifolia* gum, tragacanth gum, karaya gum, pectin, gum arabic, xanthan gum, gellan gum, starch, konjak mannan, galactomannan, funoran, acetan gum, whelan, rhamsan, furcellaran, succinoglycan, scleroglycan, schizophyllan, tamarind gum, curdlan, carrageenan, pullulan and dextran. Two of them may be used in combination or they may be used in combination with the above pig hide gelatin. These hydrophilic polymers may be processed natural products. Of these, particularly preferred are pullulan, carrageenan, and dextran, and particularly preferred is carrageenan.

The pig hide gelatin, pig bone gelatin, and fish gelatin mean proteins obtained by hot-water extraction of proteins obtained starting from pig hide, pig bone, and fish, respectively. The pig hide gelatin, pig bone gelatin, and fish gelatin of the invention can be purified by treating pig hide, pig bone, Lateolabrax, cod, tuna, a deep-sea fish, or the like with an acid or alkali, followed by extraction in water under heating and subsequent an ion-exchange treatment step.

The pig hide gelatin, pig bone gelatin, fish gelatin, or a natural hydrophilic polymer can be transformed into a lower-molecular-weight one by enzymatic treatment or the like. Thus, the average molecular weight can be suitably selected but is usually 10 to 5,000,000, preferably 10,000 to 5,000, 000, more preferably 10,000 to 2,500,000, further preferably 10,000 to 1,000,000, and particularly preferably about 10,000 to 500,000.

The capsule film for use in the capsule preparation of the invention may contain not only the raw material derived from the above specific animal or plant but also an oil and fat, a polyhydric alcohol, a surfactant, an antioxidant, a colorant, a fragrant, and the like. There may be mentioned natural oils such as evening primrose oil, soybean oil, safflower oil, olive oil, germ oil, rape seed oil, sunflower seed oil, peanut oil, cotton seed oil, rice bran oil, and cocoa butter and hardened oils thereof, and glycerides (glyceride, diglyceride, and triglyceride) of fatty acids, etc. as the oils and fats; polyethylene glycol, propylene glycol, glycerin, sorbitol, etc. as the polyhydric alcohols; nonionic surfactants such as sorbitan fatty acid esters and polyglycerin fatty acid esters as the surfactants; and carotinoid pigments, anthocyanin pigments, cacao pigment, anthranone pigments, caramel pigment, etc. as the pigments. Of these, in view of improving stability of the capsule preparation, the addition of the oil and fat, the polyhydric alcohol, the surfactant, and the natural pigment to the capsule film is preferred.

Since the antioxidant substance powder is thus satisfactory in not only transparency and dispersion stability but also storage stability of the ingredients, storage stability of the particle size, and storage stability as an emulsion, it is preferred to apply the powder to food compositions, cosmetic compositions, and pharmaceutical compositions.

As foods, drinks and frozen desserts may be mentioned, as cosmetics, skin cosmetics (lotions, essences, emulsions, creams, etc.), lipsticks, sunscreens, and makeup cosmetics may be mentioned, and as pharmaceuticals, nutrition supplement drinks and revitalizers may be mentioned, without limitation thereto.

Moreover, the above food compositions, cosmetic compositions, and pharmaceutical compositions can be obtained by mixing the antioxidant substance powder and optional ingredient(s) capable of being added for achieving desired purposes in a usual manner.

The antioxidant substance powder may be mixed with the other ingredients in a powdered form or after re-dissolution in an aqueous medium depending on the forms of objective various product compositions.

The amount of the antioxidant substance powder to be used for foods, cosmetics, and medicines varies depending on the kind and purpose of the product and is not categorically defined but the powder can be added and used so that the amount falls within the range of 0.01 to 10% by mass, preferably 0.05 to 5% by mass.

When the amount is 0.01% by mass or more, the exhibition of an objective effect can be expected, and a suitable effect can be efficiently exhibited in many cases when the amount is 10% by mass or less.

The antioxidant substance powder can be stored for a long period of time as a powder and particularly, when it is re-dissolved and used in water-soluble products, e.g., drinks (in the case of foods) and lotions, essences, emulsions, cream packs/masks, packs, cosmetics for hair washing, fragrance cosmetics, liquid body detergents, UV care cosmetics, deodorant cosmetics, oral care cosmetics, etc, (in the case of cosmetics), translucent products are obtained and also occurrence of inconvenient phenomena such as precipitation, sedimentation, and neckling of insoluble matter under severe conditions including long-term storage or sterilization can be suppressed.

The antioxidant substance powder of the invention further contains the other ingredient(s). For example, an oil and fat, a polyhydric alcohol, an organic acid, a surfactant, an antioxidant, a preservative, a sugar, a starch, crystalline cellulose, a sweetener, a colorant, a fragrant, and the like may be incorporated. Of these, an oil and fat and a polyhydric alcohol are useful. As the oil and fat, there may be mentioned natural oils such as evening primrose oil, soybean oil, safflower oil, olive oil, germ oil, rape seed oil, sunflower seed oil, peanut oil, cotton seed oil, rice bran oil, and cocoa butter and hardened oils thereof, and glycerides (glyceride, diglyceride, and triglyceride) of fatty acids, and the like, but particularly preferred is evening primrose oil. There may be mentioned polyethylene glycol, propylene glycol, glycerin, sorbitol, etc. as the polyhydric alcohols; citric acid, succinic acid, tartaric acid, aspartic acid, lactic acid, malic acid, malonic acid, fumaric acid, maleic acid, etc. as organic acids; ascorbic acid, sodium ascorbate, ascorbic acid stearic acid ester, sodium ascorbate stearate, ascorbic acid palmitic acid ester, sulfite salts, bisulfite salts, sulfur dioxide, calcium disodium EDTA, erythorbic acid, sodium erythorbate, etc. as antioxidants; and benzoic acid or salts thereof, sorbic acid or salts thereof, butyl p-oxybenzoate, isobutyl p-oxybenzoate, isopropyl p-oxybenzoate, ethyl p-oxybenzoate, etc. as preservatives.

Moreover, the powder may further contain at least one selected from vitamin K's, threonine, methionine, phenylalanine, tryptophan, lysine, glycine, alanine, asparagine, glutamine, serine, cysteine, cystine, thyronine, proline, hydroxyproline, aspartic acid, glutamic acid, hydroxylysine, arginine, ornithine, histidine, taurine, collagen, glucosamine, acetylglucosamine, hyaluronic acid, biotin, whey peptides, soybean peptides, loyal jelly, γ-oryzanol, orotic acid, rutin, hesperidin, carnitine, carnitine chloride, or salts thereof.

Embodiment

The following will describe the invention with reference to Examples but the invention is not limited thereto. In this connection, "part(s)" and "%" in the following description are based on mass unless otherwise stated.

EXAMPLE 1

Preparation of Emulsion Composition EM-1

The emulsion composition EM-1 was prepared according to the following composition and the following production process.

<Composition>

| (Ingredients) | (% by mass) |
|---|---|
| (1) *Haematococcus alga* pigment (content of astaxanthins: 20% by mass)*1 | 2.8 |
| (2) Mixed tocopherol*2 | 1.1 |
| (3) Sucrose lauric acid ester*3 | 2.6 |
| (4) Polyglyceryl laurate-10*4 | 0.8 |
| (5) Lecithin*5 | 0.7 |
| (6) Inulin*6 | 12.0 |
| (7) $H_2O$ | 80.0 |

*1ASTOTS-S: manufactured by Takedashiki Co., Ltd.
*2Riken E oil 800: manufactured by Riken Vitamin Co., Ltd.
*3RYOTO Sugar Ester L-1695: manufactured by Mitsubishi-kagaku Food Corporation
*4NIKKOL Decaglyn 1-L: Nikko Chemicals Co., Ltd.
*5Resion P: manufactured by Riken Vitamin Co., Ltd.
*6Fuji FF: Fuji Nihon Seito Corporation Preparation of Oil-soluble Antioxidant Substance Powder PW-1

(A) The above ingredients (1) and (2) were weighed into a vessel and heated and mixed under stirring in a constant-temperature chamber at 70° C. and, after thorough mixing was confirmed, the whole was maintained at 70° C. to obtain a mixture A.

(B) The above ingredients (3) to (7) were weighed into a vessel and heated and mixed under stirring in a constant-temperature chamber at 70° C. and, after thorough mixing was confirmed, the whole was maintained at 70° C. to obtain a mixture B.

(C) The mixture A was added to the mixture B and the whole was mixed and homogeneously emulsified. As an emulsifier, a homogenizer (manufactured by SMT Company) was used and stirring was performed at 10,000 rounds per minute for 5 minutes to obtain a mixture C.

(D) The mixture C was subjected to emulsification operation under a pressure of 240 MPa at a liquid temperature of 45° C. using a high-pressure homogenizer (ultimizer HJP-25003: manufactured by Sugino Machine Limited) to obtain an emulsion composition.

The resulting emulsion composition was passed through a spray drier (ADL310: manufactured by Yamato Scientific Co., Ltd.) at a rate of 10 mL per minute to be spray-dried under the flow of air at 140° C., thereby an antioxidant substance powder PW-1 being prepared.

Preparation of Powder Composition

The powder PW-1 was mixed with a water-soluble antioxidant substance (L-ascorbic acid (V.C., manufactured by Wako Pure Chemical Industries, Ltd.)) and an antioxidant mineral to prepare samples 101 to 104, and also mixtures 105 to 107 with an oil-soluble antioxidant substance (*Haematococcus* alga pigment) which had not been powdered were prepared.

every 2 to 4 hours within 24 hours after administration. After blood collection, blood astaxanthin concentration was measured by high performance liquid chromatography and body absorption was calculated. Integrated values of the blood concentration with time are shown in Table 2 as relative values, the value of the sample 101 being regarded as 100.

(3) Body Absorbability of Antioxidant Mineral

Furthermore, from the serum of the collected blood, analysis of zinc in the serum was carried out for the samples 101, 102, and 104 to 106 and analysis of selenium in the serum was carried out for the samples 103, 104, and 107, both by atomic absorption photometry.

The amounts of zinc in the serum are shown in Table 2 as relative values, the value of the sample 101 being regarded as 100. Moreover, the amounts of selenium in the serum are shown in Table 2 as relative values, the value of the sample 103 being regarded as 100.

(4) Storage Stability

The samples 101 to 107 were each divided into two portions. One portion was charged into a 10 g glass vial and stored at 50° C. for 7 days. Thereafter, for samples 101 to 104 obtained by dissolving 1 g of the powder composition in 999

TABLE 1

| | | | % by mass | | | | | |
|---|---|---|---|---|---|---|---|---|
| Sample No. | PW-1 | *Haematococcus* alga pigment *1 | Vitamin C | Zinc gluconate *2 | Zinc yeast *3 | Selenium yeast *4 | Manganese yeast *5 | Remarks |
| 101 | 40 | — | 30 | 30 | — | — | — | Invention |
| 102 | 40 | — | 30 | — | 30 | — | — | Invention |
| 103 | 40 | — | 30 | — | 10 | 10 | 10 | Invention |
| 104 | 40 | — | — | 30 | — | 10 | 20 | Comparative Example |
| 105 | — | 40 | 30 | 30 | — | — | — | Comparative Example |
| 106 | — | 40 | 30 | — | 30 | — | — | Comparative Example |
| 107 | — | 40 | 30 | — | 10 | 10 | 10 | Comparative Example |

*1 *Haematococcus alga* pigment: an oil containing astaxanthins, content: 3% by mass, manufactured by Takedashiki Co., Ltd., prepared by diluting a 10% oil with safflower oil to a 3% one
*2 zinc gluconate: manufactured by Wako Pure Chemical Industries, Ltd., 97%
*3 to *5 various mineral yeasts: manufactured by Lallemond Company Individual properties of the samples 101 to 107 were evaluated as follows.

(1) Dispersibility

In accordance to the method described in Japanese Pharmacopoeia, 7.0 ml of hydrochloric acid and water were added to 2.0 g of sodium chloride and the whole was dissolved each other to prepare 1000 ml of an artificial gastric juice. Under stirring, 2 g of each sample was added thereto and solubility and dispersibility were observed.

The dispersibility was scored under the following standard. The results are shown in Table 2.

4: sample is homogeneously dispersed

3: slight insoluble matter is observed but sample is dispersed

2: sample is dispersed but many insoluble ingredient particles are observed

1: sample is separated and not at all dispersed (2) Body Absorbability of Oil-soluble Antioxidant Substance An analyte solution was prepared by dissolving each of the above samples 101 to 107 so that astaxanthin concentration was 0.2%.

The solution was orally administrated to a rat in a constant amount per body weight (10 ml/kg) and blood was collected g of water, measurement of spectral absorption was performed on a spectrophotometer (ND-1000: manufactured by Nanodrop Company).

For the sample 105 to 107, 1 g of the composition was dissolved in 60% aqueous ethanol solution and then subjected to the measurement of spectral absorption.

The absorbance at 479 nm before storage was represented by Ab0 and the absorbance at 479 nm after storage by Ab1, the change rate being determined. In the case where storage stability is bad, Ab1 becomes larger than Ab0, so that the change rate is deflected to a large value.

Change rate(%)=(Ab0−Ab1)/Ab0×100    Equation

Scoring was performed according to the following standard. The results are shown in Table 2.

4: within 10%

3: more than 10% and within 20% (practically allowable)

2: more than 20% and within 50%

1: more than 50%

(5) Measurement of 8-hydroxydeoxyguanosine in Urine before and after Administration of Antioxidant Substance This is a method wherein 8-hydroxydeoxyguanosine excreted into urine is used as a biomarker reflecting change of living body induced by active oxygen.

Each of the samples 101 to 107 were ingested in an amount of 1 g per day for 4 weeks by 5 healthy adult men and the amounts of 8-OHdG (8-hydroxydeoxyguanosine) excreted before and after ingestion were measured. For the analysis of 8-OHdG in urine, an ELISA kit (Japan Institute for the Control of Aging) was used. The ratios of the amount of 8-OHdG excreted after 4-week ingestion to the value before ingestion are shown in Table 2. It is considered that a smaller value shows decrease in active oxygen-induced damage by the action of the antioxidant ingredient.

Furthermore, it was found that the amount of 8-OHdG excreted was decreased by the ingestion of the sample of the invention and oxidation damage in the body was reduced.

EXAMPLE 2

The water-soluble antioxidant substance, an antioxidant mineral, and the powder PW-1 were mixed in the ratio shown in Table 3 to prepare samples 111 to 113, and also mixtures 121 to 123 with an oil-soluble antioxidant substance (OIL-A: an oil containing astaxanthins, content 10% by mass, manufactured by Takedashiki Co., Ltd.) which had not been powdered were prepared.

TABLE 2

| Sample No. | Dispersibility | Body absorption of oil-soluble antioxidant substance | Body absorption of zinc | Body absorption of selenium | Storage stability | Secreted amount of 8-OHdG (%) | Remarks |
|---|---|---|---|---|---|---|---|
| 101 | 3 | 100 | 100 | — | 3 | 77 | Invention |
| 102 | 4 | 104 | 102 | — | 4 | 78 | Invention |
| 103 | 4 | 103 | — | 100 | 4 | 75 | Invention |
| 104 | 4 | 77 | 90 | 92 | 3 | 97 | Comparative Example |
| 105 | 1 | 42 | 75 | — | 2 | 95 | Comparative Example |
| 106 | 1 | 44 | 58 | — | 2 | 98 | Comparative Example |
| 107 | 1 | 41 | — | 51 | 2 | 96 | Comparative Example |

As is apparent from Table 2, the samples 101 to 103 all are excellent in dispersibility and body absorbability as compared with the samples 105 to 107 wherein the oil-soluble antioxidant substance is not in a powder form. Moreover, body absorbability of the oil-soluble antioxidant substance is improved as compared with the comparative example 104. Also, body absorbability of zinc and selenium is improved by the invention. When the samples 101, 102, 105, and 106 were compared, it was found that this effect was remarkable when yeast mineral was used.

TABLE 3

| Sample No. | Oil-soluble antioxidant substance | Vitamin C | Oil-coated Vitamin C *2 | Copper gluconate *3 | Copper yeast *4 | Cyclodextrin-included thioctic acid *5 | Remarks |
|---|---|---|---|---|---|---|---|
| 111 | PW-1 30 | 30 | — | 20 | — | 20 | Invention |
| 112 | PW-1 30 | — | 30 | 20 | — | 20 | Invention |
| 113 | PW-1 30 | — | 30 | — | 20 | 20 | Invention |
| 121 | OIL-A 20 | 30 | — | 20 | — | 20 | Comparative Example |
| 122 | OIL-A 20 | — | 30 | 20 | — | 20 | Comparative Example |
| 123 | OIL-A 20 | — | 30 | — | 20 | 20 | Comparative Example |

*1 vitamin C: manufactured by Wako Pure Chemical Industries, Ltd.
*2 oil-coated vitamin C (V.C.): content 80% by mass, manufactured by NOF Corporation
*3 copper gluconate: manufactured by Wako Pure Chemical Industries, Ltd.
*4 copper yeast: manufactured by Lallemond Company
*5 cyclodextrin-included thioctic acid, content 20% by mass: manufactured by Tateyama Kasei Individual properties of the samples 111 to 113 and 121 to 123 were evaluated as follows.

(1) Dispersibility

In accordance to the method described in Japanese Pharmacopoeia, 7.0 ml of hydrochloric acid and water were added to 2.0 g of sodium chloride and the whole was dissolved each other to prepare 1000 ml of an artificial gastric juice. Under stirring, 2.0 g of each sample was added thereto and solubility and dispersibility were observed.

The dispersibility was scored according to the following standard. The results are shown in Table 4.

4: sample is homogeneously dispersed
3: slight insoluble matter is observed but sample is dispersed
2: sample is dispersed but many insoluble ingredient particles are observed
1: sample is separated and not at all dispersed (2) Storage Stability The samples 111 to 113 and 121 to 123 were each divided into two portions. One portion was charged into a 10 g glass vial and stored at 40° C. under 75% RH for 7 days. Thereafter, for samples 111 to 113 obtained by dissolving 1 g of the powder composition in 999 g of water, measurement of spectral absorption was performed on a spectrophotometer (ND-1000: manufactured by Nanodrop Company).

For the sample 121 to 123, 1 g of the composition was dissolved in 60% aqueous ethanol solution and then subjected to the measurement of spectral absorption.

The absorbance before storage was represented by Ab0 and the absorbance after storage by Ab1, the change rate being determined. In the case where storage stability is bad, Ab1 becomes larger than Ab0, so that the change rate is deflected to a large value.

$$\text{Change rate}(\%) = (Ab0 - Ab1)/Ab0 \times 100 \quad \text{Equation}$$

Scoring was performed according to the following standard. The results are shown in Table 4.

4: within 10%
3: more than 10% and within 20% (practically allowable)
2: more than 20% and within 50%
1: more than 50%

Furthermore, color after storage was visually evaluated.

TABLE 4

| Sample No. | Dispersibility | Storage stability | Color after storage | Remarks |
|---|---|---|---|---|
| 111 | 4 | 3 | Black particles are slightly formed (tolerance level) | Invention |
| 112 | 4 | 3 | Black particles are slightly formed (tolerance level) | Invention |
| 113 | 4 | 4 | Hardly changed | Invention |
| 121 | 1 | 2 | Changed to black | Comparative Example |
| 122 | 1 | 2 | Changed to black | Comparative Example |
| 123 | 1 | 2 | Changed to black | Comparative Example |

As is apparent from Table 4, the samples 111 to 113 all are obviously excellent in dispersibility and storage stability as compared with the samples 121 to 123 wherein the oil-soluble antioxidant substance is not in a powder form. Particularly, the sample 113 of the invention affords the best result in view of stability after storage.

EXAMPLE 3

Then, using PW-1 obtained in Example 1, a hard capsule type supplement was prepared according to the following composition and production method.

| | |
|---|---|
| (1) PW-1 of Example 1 | 50 mg |
| (2) Oil-coated V.C. | 30 mg |
| (3) Cyclodextrin-included thioctic acid | 50 mg |
| (4) PW-2 of Example 2 | 20 mg |
| (5) Selenium yeast | 10 mg |
| (6) Zinc yeast | 25 mg |
| (7) Manganese yeast | 10 mg |
| (8) Lycopene powder | 10 mg |
| (9) Crystalline cellulose | 40 mg |
| (10) Microparticulate silicon dioxide | 5 mg |
| Total | 250 mg |

The above ingredients (1) to (10) were mixed and then a supplement filled into a hard capsule colored with caramel pigment was prepared. The resulting supplement was excellent in storage stability of the oil-soluble antioxidant substance.

Industrial Applicability

The present invention provides a powder composition containing antioxidant substances, which improves absorbability into the body and storage stability of the antioxidant substances.

Namely, according to the powder composition of the invention, ingredients which care antioxidation balance in the body can be ingested at once and also absorption efficiency is good. As compared with the case of taking a plurality of single-ingredient supplements, the amount of the ingredients may be small and also degree of deterioration of the ingredients and the color is little.

The entire disclosure of each and every foreign patent application from which the benefit of foreign priority has been claimed in the present application is incorporated herein by reference, as if fully set forth.

The invention claimed is:

1. A powder composition, comprising:
(A) an oil-soluble antioxidant substance powder;
(B) a water-soluble antioxidant substance powder;
(C) at least one of zinc, selenium, manganese and copper, and
(D) a cyclodextrin/thioctic acid complex powder,
wherein the oil-soluble antioxidant substance powder (A), the water-soluble antioxidant substance powder (B), the at least one of zinc, selenium, manganese and copper (C), and the cyclodextrin/thioctic acid complex powder (D) coexist;
the oil-soluble antioxidant substance powder (A) contains a carotinoid pigment, the carotinoid pigment being a natural extract containing astaxanthin or an ester of astaxanthin, and
the water-soluble antioxidant substance powder (B) contains at least one of vitamin C, a catechin and a flavonoid.

2. The powder composition according to claim 1, wherein the oil-soluble antioxidant substance (A) is a powder composition obtained by drying an emulsion composition containing: (a) at least one of a sucrose fatty acid ester and a polyglycerin fatty acid ester; and (b) a phospholipid, wherein mass composition ratios of (a) and (b) are the same or the mass composition ratio of (a) is larger than the mass composition ratio of (b).

3. The powder composition according to claim 1, wherein the water-soluble antioxidant substance (B) is an oil-coated powder.

4. The powder composition according to claim 1, comprising:
a mineral yeast that contains (C) the at least one of zinc, selenium, manganese and copper.

5. The powder composition according to claim 1, wherein the oil-soluble antioxidant substance powder is contained in an amount of 6 to 70% by mass, the water-soluble antioxidant substance is contained in an amount of 10 to 80% by mass, and thioctic acid is contained in an amount of 2 to 60% by mass, based on the total amount of the powder composition.

6. The powder composition according to claim 1, wherein the oil-soluble antioxidant substance powder is contained in an amount of 20 to 50% by mass, the water-soluble antioxidant substance is contained in an amount of 20 to 60% by mass, and thioctic acid is contained in an amount of 10 to 50% by mass, based on the total amount of the powder composition.

\* \* \* \* \*